US012226566B2

(12) United States Patent
Askem et al.

(10) Patent No.: US 12,226,566 B2
(45) Date of Patent: Feb. 18, 2025

(54) DUAL MODE NEGATIVE PRESSURE SOURCE OPERATION FOR PROVISION OF NEGATIVE PRESSURE WOUND THERAPY

(71) Applicant: T.J.Smith and Nephew, Limited, Hull (GB)

(72) Inventors: Ben Alan Askem, Leeds (GB); David Michael Elder, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 247 days.

(21) Appl. No.: 17/919,700

(22) PCT Filed: Apr. 23, 2021

(86) PCT No.: PCT/EP2021/060655
§ 371 (c)(1),
(2) Date: Oct. 18, 2022

(87) PCT Pub. No.: WO2021/214286
PCT Pub. Date: Oct. 28, 2021

(65) Prior Publication Data
US 2023/0145353 A1 May 11, 2023

(30) Foreign Application Priority Data
Apr. 23, 2020 (GB) ...................... 2005928

(51) Int. Cl.
*A61M 1/00* (2006.01)
(52) U.S. Cl.
CPC .............. *A61M 1/966* (2021.05); *A61M 1/75* (2021.05); *A61M 2205/3344* (2013.01)

(58) Field of Classification Search
CPC .................... A61M 1/966; A61M 1/75; A61M 2205/3344; A61M 2205/3317; A61M 1/73
See application file for complete search history.

(56) References Cited

U.S. PATENT DOCUMENTS 8,157,792 B2 4/2012 Dolliver et al.
8,858,517 B2 10/2014 Pan et al.
(Continued)

FOREIGN PATENT DOCUMENTS

EP 3187202 A1 * 7/2017 .......... A61M 1/0088
WO WO-9401154 A1 * 1/1994 .......... A61M 13/003
(Continued)

OTHER PUBLICATIONS

International Search Report and Written Opinion for Application No. PCT/EP2021/060655, mailed on Jun. 28, 2021, 20 pages.
(Continued)

*Primary Examiner* — Ariana Zimbouski
*Assistant Examiner* — Eric Rassavong
(74) *Attorney, Agent, or Firm* — Knobbe, Martens, Olson & Bear, LLP

(57) ABSTRACT

A negative pressure source can be fluidically connected to the wound dressing, the wound dressing can be positioned to cover at least a portion of the wound, and the negative pressure source can be controlled to supply negative pressure to the wound via the fluid flow path. An actuator of the negative pressure source can be controlled to operate in a dual mode by transitioning between a proportional-integral (PI) control or proportional-integral-derivative (PID) control and a pulsed control. Stalling of the actuator can be prevented, and therapy can be provided without interruptions.

21 Claims, 7 Drawing Sheets

(56) References Cited

U.S. PATENT DOCUMENTS

| | | |
|---|---|---|
| 9,474,838 B2 | 10/2016 | Locke et al. |
| 10,124,093 B1 * | 11/2018 | Francis .................. A61M 1/96 |
| 10,434,227 B2 | 10/2019 | Boynton et al. |
| 11,376,357 B2 | 7/2022 | Aarestad et al. |
| 11,478,383 B2 | 10/2022 | Severns et al. |
| 11,614,170 B2 | 3/2023 | Tumey et al. |
| 2003/0040687 A1 | 2/2003 | Boynton et al. |
| 2003/0220609 A1 * | 11/2003 | Childers ............... A61M 1/166 604/28 |
| 2011/0015593 A1 | 1/2011 | Svedman et al. |
| 2017/0165406 A1 * | 6/2017 | Chien .................... A61M 1/75 |
| 2017/0296715 A1 | 10/2017 | Weston et al. |
| 2019/0030223 A1 * | 1/2019 | Lin ...................... A61M 3/022 |
| 2019/0125942 A1 | 5/2019 | Francis, Jr. et al. |
| 2019/0175800 A1 | 6/2019 | Askem |
| 2019/0231939 A1 | 8/2019 | Askem et al. |
| 2019/0374689 A1 | 12/2019 | Coulthard et al. |
| 2022/0001100 A1 | 1/2022 | Pratt et al. |

FOREIGN PATENT DOCUMENTS

| | | | | |
|---|---|---|---|---|
| WO | WO-2008100440 A1 * | 8/2008 | .......... | A61M 1/0027 |
| WO | WO-2009089390 A2 * | 7/2009 | .......... | A61M 1/0027 |
| WO | WO-2012038724 A1 * | 3/2012 | ....... | A61F 13/00068 |
| WO | WO-2013140255 A1 * | 9/2013 | .......... | A61M 1/0031 |
| WO | WO-2018164803 A1 | 9/2018 | | |
| WO | WO-2019083966 A1 * | 5/2019 | ............ | A61M 1/742 |
| WO | WO-2020018328 A1 | 1/2020 | | |
| WO | WO-2020061334 A1 | 3/2020 | | |
| WO | WO-2020176331 A1 | 9/2020 | | |
| WO | WO-2020263508 A1 | 12/2020 | | |
| WO | WO-2021028773 A1 | 2/2021 | | |
| WO | WO-2021059127 A1 | 4/2021 | | |
| WO | WO-2021059209 A1 | 4/2021 | | |

OTHER PUBLICATIONS

International Preliminary Report on Patentability for Application No. PCT/EP2021/060655, mailed on Nov. 3, 2022, 13 pages.

* cited by examiner

DUAL MODE NEGATIVE PRESSURE SOURCE OPERATION FOR PROVISION OF NEGATIVE PRESSURE WOUND THERAPY

CROSS-REFERENCE TO RELATED APPLICATIONS

This application is a U.S. national stage application of International Patent Application No. PCT/EP2021/060655, filed on Apr. 23, 2021, which claims priority to U.K. Provisional Application No. 2005928.3 filed on Apr. 23, 2020, the disclosure of each of which is hereby incorporated by reference in its entirety.

TECHNICAL FIELD

Embodiments described herein relate to apparatuses, systems, and methods for the treatment of wounds, for example using dressings in combination with negative pressure wound therapy.

DESCRIPTION OF THE RELATED ART

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing.

SUMMARY

A negative pressure wound therapy device can include a source of negative pressure, a pressure sensor, and a controller. The source of negative pressure can be connected via a fluid flow path to a wound covered by a wound dressing. The source of negative pressure can be configured to supply negative pressure to the wound via the fluid flow path. The pressure sensor can be configured to measure pressure in the fluid flow path. The controller can be configured to control the source of negative pressure. The controller can be configured to determine a pressure difference between a negative pressure setpoint corresponding to desired negative pressure at the wound and pressure measured by the pressure sensor. The controller can be configured to, in response to determining that the pressure difference does not satisfy a low flow threshold indicative of an actuator of the source of negative pressure operating to provide low flow in the fluid flow path, apply to the actuator a first drive signal determined based on the pressure difference. The application of the first drive signal can cause reduction of the pressure difference. The controller can be configured to, in response to determining that the pressure difference satisfies the low flow threshold, apply a second drive signal to the actuator. The second drive signal can cause the actuator to be activated for a first period of time and deactivated for a second period of time subsequent to the first period of time.

The negative pressure wound therapy device of the preceding paragraph and/or any of the apparatuses, systems, or devices disclosed herein can include one or more of the following features. The first drive signal can cause the actuator to operate in accordance with at least one of a proportional integral (PI) control or proportional integral derivative (PID) control. The second drive signal can cause the actuator to operate in accordance with pulsed control. The first drive signal can cause the actuator to be activated for a duration of the first drive signal. The actuator can include a pump motor. The low flow threshold can correspond to stalling of the pump motor. The low flow threshold can correspond to a blockage in the fluid flow path.

A negative pressure wound therapy device can include a source of negative pressure, a pressure sensor, and a controller. The source of negative pressure can be connected via a fluid flow path to a wound covered by a wound dressing. The source of negative pressure can be configured to supply negative pressure to the wound via the fluid flow path. The pressure sensor can be configured to measure pressure in the fluid flow path. The controller can be configured to control the source of negative pressure. The controller can be configured to, responsive to a determination that a pressure difference between a desired level of negative pressure at the wound and pressure measured by the pressure sensor does not satisfy a stall threshold of the motor, operate a motor of the source of negative pressure according to a proportional integral (PI) control. The controller can be configured to, responsive to a determination that the pressure difference satisfies the stall threshold of the motor, operate the motor according to a pulsed control.

The negative pressure wound therapy device of any of the preceding paragraphs and/or any of the apparatuses, systems, or devices disclosed herein can include one or more of the following features. The stall threshold of the motor can correspond to a voltage or current level causing the motor to stall. Pulsed control can include alternating periods of activation and deactivation of the motor.

A negative pressure wound therapy device can include a source of negative pressure, a pressure sensor, and a controller. The source of negative pressure can be connected via a fluid flow path to a wound covered by a wound dressing. The source of negative pressure can be configured to supply negative pressure to the wound via the fluid flow path. The pressure sensor can be configured to measure pressure in the fluid flow path. The controller can be configured to control the source of negative pressure. The controller can be configured to, apply a first drive signal to an actuator of the source of negative pressure to cause the source of negative pressure to supply negative pressure to the wound via the fluid flow path. The controller can be configured to monitor negative pressure at the wound using the pressure sensor. The controller can be configured to adjust the first drive signal applied to the actuator based on a difference between the monitored negative pressure and a negative pressure setpoint. The controller can be configured to, responsive to a determination that a low flow threshold is satisfied, apply a second drive signal different from the first drive signal to the actuator. Application of the second drive signal can cause the actuator to continue operating to establish or maintain the negative pressure setpoint at the wound.

The negative pressure wound therapy device of any of the preceding paragraphs and/or any of the apparatuses, systems, or devices disclosed herein can include one or more of the following features. The controller can be configured to adjust the first drive signal to minimize the difference between the monitored negative pressure and the negative pressure setpoint. The controller can be configured to determine that the low flow threshold is satisfied responsive to the difference satisfying a pressure difference threshold. The controller can be configured to iteratively adjust the first drive signal. The controller can be configured to, responsive to a determination that the monitored negative pressure is smaller than a pressure threshold, cease applying the second drive signal and apply the first drive signal to the actuator. The controller can be configured to cease applying the second drive signal and apply the first drive signal responsive to a determination that the low flow threshold is no longer satisfied. The controller can be configured to apply the first drive signal at a power level that exceeds a power level associated with the low flow threshold by a threshold power level.

The negative pressure wound therapy device of any of the preceding paragraphs and/or any of the apparatuses, systems, or devices disclosed herein can include one or more of the following features. The controller can be configured to, responsive to a determination that the monitored negative pressure does not satisfy the negative pressure setpoint, continue to adjust the first drive signal based on the difference. The first drive signal can cause the actuator to operate in accordance with at least one of a proportional integral (PI) control or proportional integral derivative (PID) control. The second drive signal can cause the actuator to operate in accordance with pulsed control that alternates periods of activation and deactivation of the actuator. The actuator can include a motor. The low flow threshold can be associated with stalling of the motor.

The negative pressure wound therapy device of any of the preceding paragraphs and/or any of the apparatuses, systems, or devices disclosed herein can include one or more of the following features. The controller can be configured to apply the second drive signal at a power level that is less than maximum power level of the actuator.

Disclosed herein are methods of operating a negative pressure wound therapy device of any of the preceding paragraphs and/or any of the devices, apparatuses, or systems disclosed herein. Disclosed herein are computer-readable storage media storing instructions that, when executed by a controller of a negative pressure wound therapy device, cause the controller implement any of the methods disclosed herein.

Disclosed herein are kits that include the negative pressure wound therapy device of any of the preceding paragraphs and/or any of the devices, apparatuses, or systems disclosed herein and one or more wound dressings.

Any of the features, components, or details of any of the arrangements or embodiments disclosed in this application, including without limitation any of the apparatus embodiments and any of the negative pressure wound therapy embodiments disclosed herein, are interchangeably combinable with any other features, components, or details of any of the arrangements or embodiments disclosed herein to form new arrangements and embodiments.

DETAILED DESCRIPTION

Figure 1A:
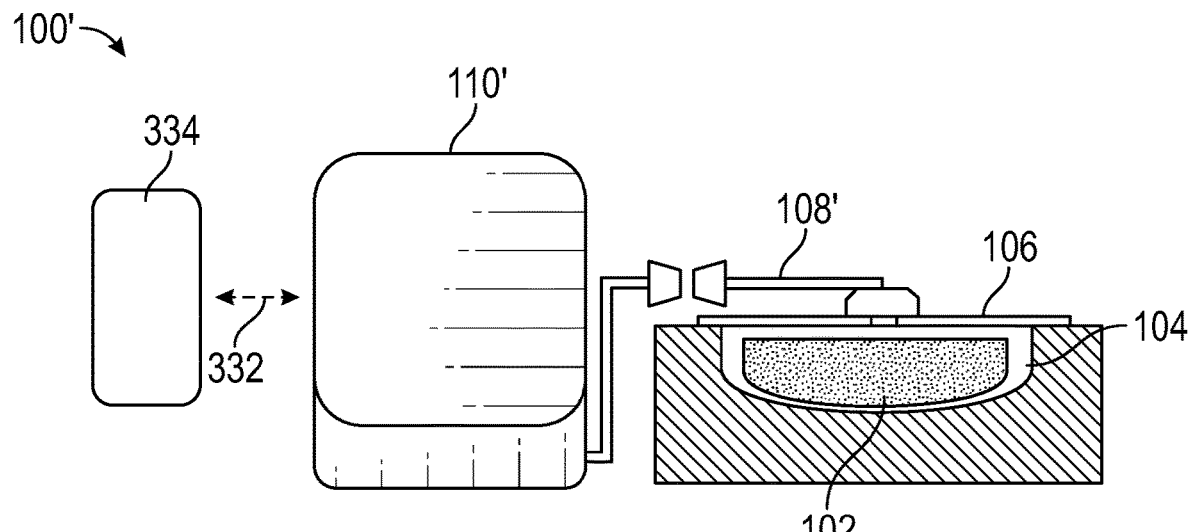
FIG. 1A illustrates a negative pressure wound therapy system.

Embodiments disclosed herein relate to systems and methods of treating and/or monitoring a wound. Some embodiments of the negative pressure wound therapy devices disclosed herein can include a negative pressure source configured to be connected and/or fluidically coupled, via a fluid flow path, to a wound covered by a wound dressing and provide negative pressure to a wound.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As used herein, reduced or negative pressure levels, such as —X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects pressure that is X mmHg below 760 mmHg or, in other words, a pressure of (760–X) mmHg. In addition, negative pressure that is "less" or "smaller" than X mmHg corresponds to pressure that is closer to atmospheric pressure (for example, —40 mmHg is less than –60 mmHg). Negative pressure that is "more" or "greater" than —X mmHg corresponds to pressure that is further from atmospheric pressure (for example, —80 mmHg is more than –60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A healthcare provider, such as a clinician, nurse, or the like, can provide a TNP prescription specifying, for example, the pressure level or time of application. However, the healing process is different for each patient and the prescription may affect the healing process in a way the clinician or healthcare provider did not expect at the time of devising the prescription. A healthcare provider may try to adjust the prescription as the wound heals (or does not heal), but such process may require various appointments that can be time consuming and repetitive. Embodiments disclosed herein provide systems, devices, or methods of efficiently adjusting TNP prescriptions and delivering effective TNP therapy.

Wound Therapy System

FIG. 1A schematically illustrates a negative pressure wound treatment system 100 (sometimes referred to as a reduced or negative pressure wound therapy system, a TNP system, or a wound treatment system). In any implementations disclosed herein, though not required, the negative pressure wound treatment system 100 can include a wound filler 102 placed on or inside a wound 104 (which may be a cavity). The wound 104 can be sealed by a wound cover 106, which can be a drape, such that the wound cover 106 can be in fluidic communication with the wound 104. The wound filler 102 in combination with the wound cover 106 can be referred to as a wound dressing. A tube or conduit 108 (also referred to herein as a flexible suction adapter or a fluidic connector) can be used to connect the wound cover 106 with a wound therapy device 110 (sometimes as a whole or partially referred to as a "pump assembly") configured to supply reduced or negative pressure. The conduit 108 can be a single or multi lumen tube. A connector 112 can be used to removably and selectively couple a conduit or tube 142 with the conduit 108.

In any of the systems disclosed herein, a wound therapy device can be canisterless, wherein, for example and without limitation, wound exudate is collected in the wound dressing or is transferred via a conduit for collection at another location. However, any of the wound therapy devices disclosed herein can include or support a canister.

Additionally, with any of the wound therapy systems disclosed herein, any of the wound therapy devices can be mounted to or supported by the wound dressing or adjacent to the wound dressing. The wound filler 102 can be any suitable type, such as hydrophilic or hydrophobic foam, gauze, inflatable bag, and so on. The wound filler 102 can be conformable to the wound 104 such that the wound filler 102 substantially fills the cavity of the wound 104. The wound cover 106 can provide a substantially fluid impermeable seal over the wound 104. The wound cover 106 can have a top side and a bottom side. The bottom side can adhesively (or in any other suitable manner) seal with the wound 104, for example by sealing with the skin around the wound 104. The conduit 108 or any other conduit disclosed herein can be formed from polyurethane, PVC, nylon, polyethylene, silicone, or any other suitable material.

The wound cover 106 can have a port (not shown) configured to receive an end of the conduit 108. In some cases, the conduit 108 can otherwise pass through or under the wound cover 106 to supply reduced pressure to the wound 104 so as to maintain a desired level of reduced pressure in the wound 104. The conduit 108 can be any suitable article configured to provide at least a substantially sealed fluid flow pathway or path between the wound therapy device 110 and the wound cover 106, so as to supply the reduced pressure provided by the wound therapy device 110 to wound 104.

The wound cover 106 and the wound filler 102 can be provided as a single article or an integrated single unit. In some cases, no wound filler is provided and the wound cover by itself may be considered the wound dressing. The wound dressing can then be connected, via the conduit 108, to a source of negative pressure of the wound therapy device 110. In some cases, though not required, the wound therapy device 110 can be miniaturized and portable, although larger conventional negative pressure sources (or pumps) can also be used.

The wound cover 106 can be located over a wound site to be treated. The wound cover 106 can form a substantially sealed cavity or enclosure over the wound. The wound cover 106 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.

The wound therapy device 110 can operate with or without the use of an exudate canister. In some cases, as is illustrated, the wound therapy device 110 can include an exudate canister. In some cases, configuring the wound therapy device 110 and conduit 108 so that the conduit 108 can be quickly and easily removed from the wound therapy device 110 can facilitate or improve the process of wound dressing or pump changes, if necessary. Any of the pump assemblies disclosed herein can have any suitable connection between the conduit 108 and the pump.

The wound therapy device 110 can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 110.

As will be described in greater detail below, the negative pressure wound treatment system 100 can be configured to provide a connection 332 to a separate or remote computing device 334. The connection 332 can be wired or wireless (such as, Bluetooth, Bluetooth low energy (BLE), Near-Field Communication (NFC), WiFi, or cellular). The remote computing device 334 can be a smartphone, a tablet, a laptop or another standalone computer, a server (such as, a cloud server), another pump device, or the like.

Figure 1B:
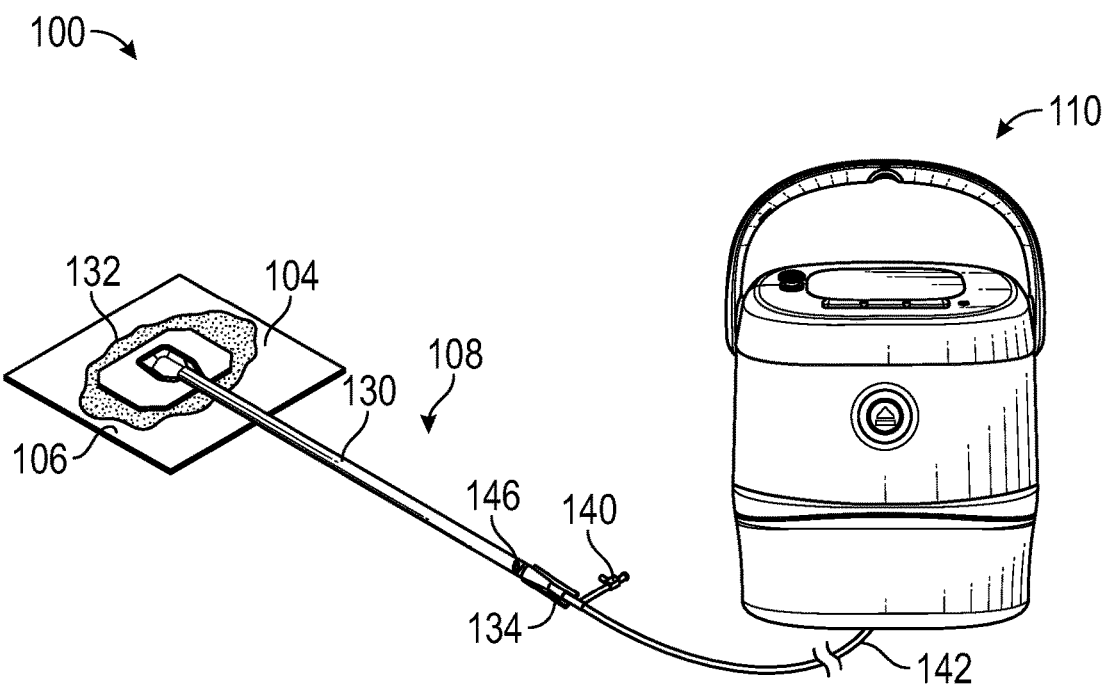
FIG. 1B illustrates another negative pressure wound therapy system.

FIG. 1B illustrates another negative pressure wound treatment system 100'. The negative pressure wound treatment system 100' can have any of the components, features, or other details of any of the other negative pressure wound treatment system disclosed herein, including without limitation the negative pressure wound treatment system 100 illustrated in FIG. 1A or the negative pressure wound treatment system 400 illustrated in FIG. 4, in combination with or in place of any of the components, features, or other details of the negative pressure wound treatment system 100' shown in FIG. 1B and/or described herein. The negative pressure wound treatment system 100' can have a wound cover 106 over a wound 104 that can seal the wound 104. A conduit 108', such as a single or multi lumen tube can be used to connect the wound cover 106 with a wound therapy device 110' (sometimes as a whole or partially referred to as a "pump assembly") configured to supply reduced or negative pressure. The wound cover 106 can be in fluidic communication with the wound 104.

With reference to FIG. 1B, the conduit 108' can have a bridge portion 130 that can have a proximal end portion and a distal end portion (the distal end portion being closer to the wound 104 than the proximal end portion, and an applicator 132 at the distal end of the bridge portion 130 forming the flexible suction adapter (or conduit) 108'. A connector 134 can be disposed at the proximal end of the bridge portion 130, so as to connect to at least one of the channels that can extend along a length of the bridge portion 130 of the conduit 108 shown in FIG. 1B. A cap 140 can be coupled with a portion of the conduit 108 and can, in some cases, as illustrated, be attached to the connector 134. The cap 140 can be useful in preventing fluids from leaking out of the proximal end of the bridge portion 130. The conduit 108' can be a Soft Port manufactured by Smith & Nephew. As mentioned, the negative pressure wound treatment system 100' can include a source of negative pressure, such as the device 110', capable of supplying negative pressure to the wound 104 through the conduit 108'. Though not required, the device 110' can also include a canister or other container for the storage of wound exudates and other fluids that can be removed from the wound.

The device 110' can be connected to the connector 134 via a conduit or tube 142. In use, the applicator 132 can be placed over an aperture formed in a cover 106 that is placed over a suitably-prepared wound or wound 104. Subsequently, with the wound therapy device 110' connected via the tube 142 to the connector 134, the wound therapy device 110' can be activated to supply negative pressure to the wound. Application of negative pressure can be applied until a desired level of healing of the wound is achieved.

The bridge portion 130 can comprise an upper channel material or layer positioned between an upper layer and an intermediate layer, with a lower channel material or layer positioned between the intermediate layer and a bottom layer. The upper, intermediate, and lower layers can have elongate portions extending between proximal and distal ends and can include a material that is fluid-impermeable, for example polymers such as polyurethane. It will of course be appreciated that the upper, intermediate, and lower layers can each be constructed from different materials, including semi-permeable materials. In some cases, one or more of the upper, intermediate, and lower layers can be at least partially transparent. In some instances, the upper and lower layers can be curved, rounded or outwardly convex over a majority of their lengths.

The upper and lower channel layers can be elongate layers extending from the proximal end to the distal end of the bridge 130 and can each preferably comprise a porous material, including for example open-celled foams such as polyethylene or polyurethane. In some cases, one or more of the upper and lower channel layers can be comprised of a fabric, for example a knitted or woven spacer fabric (such as a knitted polyester 3D fabric, Baltex 7970®, or Gehring 879®) or a nonwoven material, or terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure or vented air to the wound site, and can also confer a degree of kinking or occlusion resistance to the channel layers. In one example, the upper channel layer can include an open-celled foam such as polyurethane, and the lower channel layer can include a fabric. In another example, the upper channel layer is optional, and the system can instead be provided with an open upper channel. The upper channel layer can have a curved, rounded or upwardly convex upper surface and a substantially flat lower surface, and the lower channel layer can have a curved, rounded or downwardly convex lower surface and a substantially flat upper surface.

The fabric or material of any components of the bridge 130 can have a three-dimensional (3D) structure, where one or more types of fibers form a structure where the fibers extend in all three dimensions. Such a fabric can in some cases aid in wicking, transporting fluid or transmitting negative pressure. In some cases, the fabric or materials of the channels can include several layers of material stacked or layered over each other, which can in some cases be useful in preventing the channel from collapsing under the application of negative pressure. The materials used in some implementations of the conduit 108' can be conformable and pliable, which can, in some cases, help to avoid pressure ulcers and other complications which can result from a wound treatment system being pressed against the skin of a patient.

The distal ends of the upper, intermediate, and lower layers and the channel layers can be enlarged at their distal ends (to be placed over a wound site), and can form a "teardrop" or other enlarged shape. The distal ends of at least the upper, intermediate, and lower layers and the channel layers can also be provided with at least one through aperture. This aperture can be useful not only for the drainage of wound exudate and for applying negative pressure to the wound, but also during manufacturing of the device, as these apertures can be used to align these respective layers appropriately.

In some implementations, a controlled gas leak 146 (sometimes referred to as gas leak, air leak, or controlled air leak) can be disposed on the bridge portion 130, for example at the proximal end thereof. This air leak 146 can comprise an opening or channel extending through the upper layer of the bridge portion 130, such that the air leak 146 is in fluidic communication with the upper channel of the bridge portion 130. Upon the application of suction to the conduit 108, gas (such, as air) can enter through the gas leak 146 and move from the proximal end of the bridge portion 130 to the distal end of the bridge portion along the upper channel of the bridge portion 130. The gas can then be suctioned into the lower channel of the bridge portion 130 by passing through the apertures through the distal ends of the upper, intermediate, and lower layers.

The air leak 146 can include a filter. Preferably, the air leak 146 is located at the proximal end of the bridge portion 130 so as to minimize the likelihood of wound exudate or other fluids coming into contact and possibly occluding or interfering with the air leak 146 or the filter. In some instances, the filter can be a microporous membrane capable of excluding microorganisms and bacteria, and which may be able to filter out particles larger than 45 μm. Preferably, the filter can exclude particles larger than 1.0 μm, and more preferably, particles larger than 0.2 μm. Advantageously, some implementations can provide for a filter that is at least partially chemically-resistant, for example to water, common household liquids such as shampoos, and other surfactants. In some cases, reapplication of vacuum to the suction adapter or wiping of the exposed outer portion of the filter may be sufficient to clear any foreign substance occluding the filter. The filter can be composed of a suitably-resistant polymer such as acrylic, polyethersulfone, or polytetrafluoroethylene, and can be oleophobic or hydrophobic. In some cases, the gas leak 146 can supply a relatively constant gas flow that does not appreciably increase as additional negative pressure is applied to the conduit 108'. In instances of the negative pressure wound treatment system 100 where the gas flow through the gas leak 146 increases as additional negative pressure is applied, preferably this increased gas flow will be minimized and not increase in proportion to the negative pressure applied thereto. Further description of such bridges, conduits, air leaks, and other components, features, and details that can be used with any implementations of the negative pressure wound treatment systems disclosed herein are found in U.S. Pat. No. 8,801,685, which is incorporated by reference in its entirety as if fully set forth herein.

Any of the wound therapy devices (such as, the device 110 or 110') disclosed herein can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. Intermittent therapy can be delivered between low and high negative pressure set points (sometimes referred to as setpoint). Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 102 can be inserted into the cavity of the wound 104, and wound cover 106 can be placed so as to seal the wound 104. The wound therapy device 110' can provide negative pressure to the wound cover 106, which can be transmitted to the wound 104 via the wound filler 102. Fluid (such as, wound exudate) can be drawn through the conduit 108' and stored in a canister. In some cases, fluid is absorbed by the wound filler 102 or one or more absorbent layers (not shown).

Wound dressings that can be utilized with the pump assembly and systems of the present application include Renasys-F, Renasys-G, Renasys AB, and Pico Dressings available from Smith & Nephew. Further description of such wound dressings and other components of a negative pressure wound therapy system that can be used with the pump assembly and systems of the present application are found in U.S. Patent Publication Nos. 2012/0116334, 2011/0213287, 2011/0282309, 2012/0136325, U.S. Pat. No. 9,084,845, and International App. No. PCT/EP2020/078376, each of which is incorporated by reference in its entirety as if fully set forth herein. In some cases, other suitable wound dressings can be utilized.

Figure 2A:
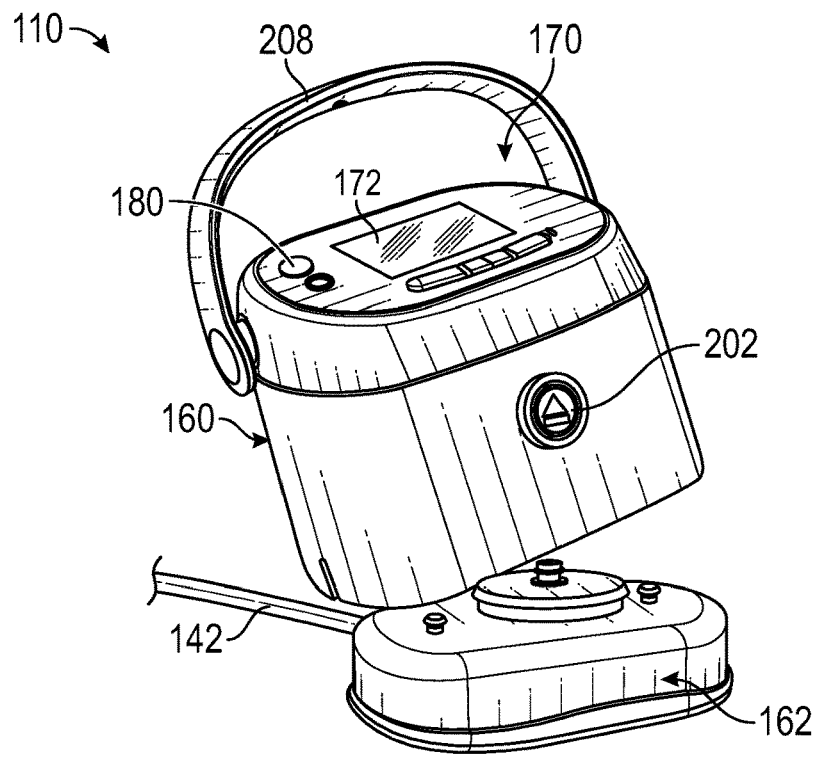
FIG. 2A is an isometric view of a negative pressure wound therapy device and canister, showing the canister detached from the pump assembly of the device.
Figure 2B:
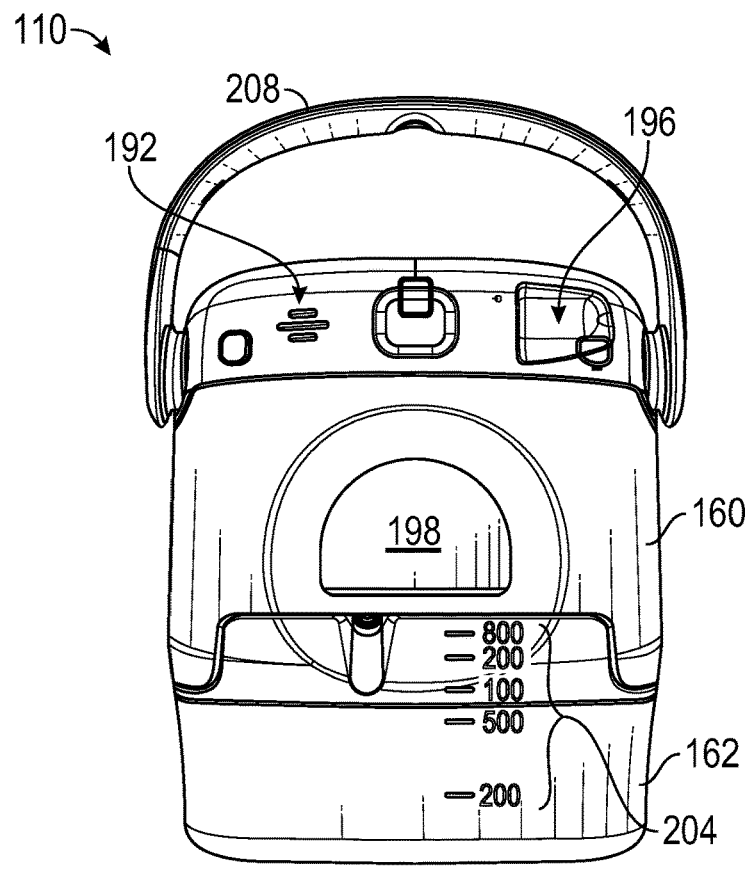
FIG. 2B is a back view of the negative pressure wound therapy device shown in FIG. 2A.
Figure 2C:
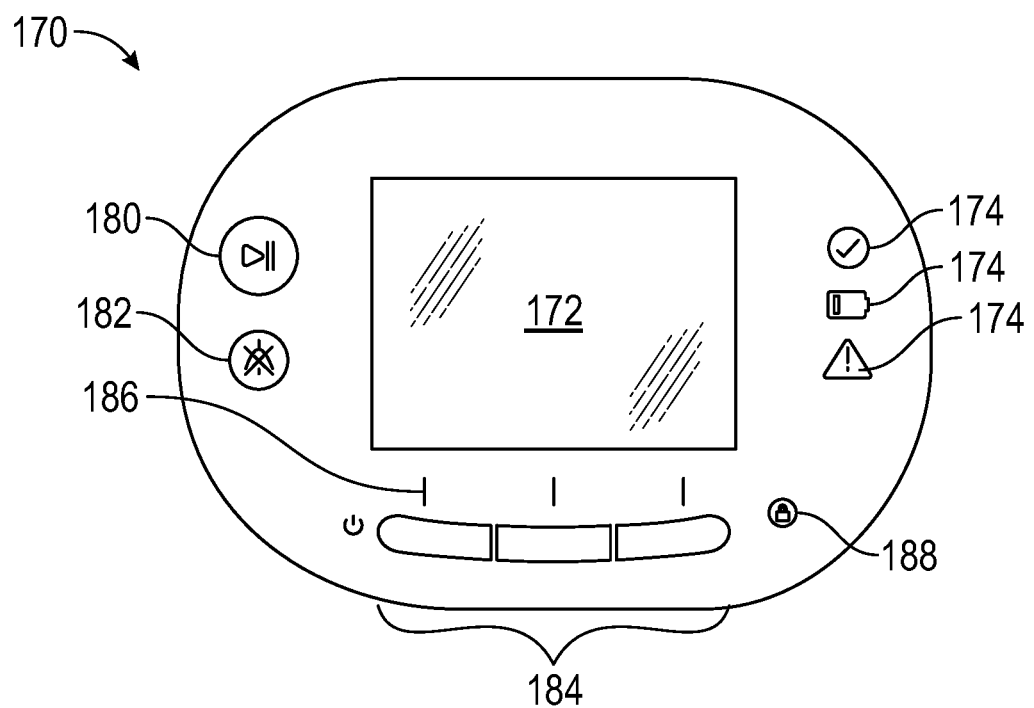
FIG. 2C illustrates a top surface of the negative pressure wound therapy device shown in FIG. 2A, showing a user interface.

FIGS. 2A-2C show the negative pressure wound therapy device 110'. As illustrated, a pump assembly 160 and canister 162 can be connected, thereby forming the wound therapy device 110'. With reference to FIG. 2C, the pump assembly 160 can include an interface panel 170 having a display 172, one or more indicators 174, or one or more controls or buttons, including, for example and without limitation, a therapy start and pause button 180 or an alarm/alert mute button 182. The interface panel 170 can have one or more input controls or buttons 184 (three being shown) that can be used to control any functions of the pump assembly 160 or the interface panel 170. For example and without limitation, one or more of the buttons 184 can be used to turn the pump assembly 160 on or off, to start or pause therapy, to operate and monitor the operation of the pump assembly 160, to scroll through menus displayed on the display 172, or to control or perform other functions. In some cases, the command buttons 184 can be programmable, and can be made from a tactile, soft rubber.

Additionally, the interface panel 170 can have visual indicators 186 that can indicate which of the one or more buttons 184 is active. The interface panel 170 can also have a lock/unlock control or button 188 that can be configured to selectively lock or unlock the functionality of the various buttons (e.g., buttons 184) or the display 172. For example, therapy setting adjustment can be locked/unlocked via the lock/unlock control 188. When the lock/unlock button 188 is in the locked state, depressing one or more of the various other buttons or the display will not cause the pump assembly 160 to change any display functions or performance functions of the device. This way, the interface panel 170 will be protected from inadvertent bumping or touching of the various buttons or display. The interface panel 170 can be located on an upper portion of the pump assembly 160, for example and without limitation on an upward facing surface of the pump assembly 160.

The display 172, which can be a screen such as an LCD screen, can be mounted in a middle portion of the interface panel 170. The display 172 can be a touch screen display. The display 172 can support playback of audiovisual (AV) content, such as instructional videos, and render a number of screens or graphical user interfaces (GUIs) for configuring, controlling, and monitoring the operation of the pump assembly 160.

The one or more indicators 174 can be lights (such as, LEDs) and can be configured to provide a visual indication of alarm conditions and or a status of the pump. For example and without limitation, the one or more indicators 174 can be configured to provide a visual indication of a status of the pump assembly 160 or other components of the negative pressure wound treatment system 100', including without limitation the conduit 108' or the wound cover 106 (such as, to provide an indication of normal operation, low battery, a leak, canister full, blockage, overpressure, or the like). Any one or more suitable indicators can be additionally or alternatively used, such as visual, audio, tactile indicator, and so on.

FIG. 2B shows a back or rear view of the wound therapy device 110' shown in the FIG. 2A. As shown, the pump assembly 160 can include a speaker 192 for producing sound. For example and without limitation, the speaker 192 can generate an acoustic alarm in response to deviations in therapy delivery, non-compliance with therapy delivery, or any other similar or suitable conditions or combinations thereof. The speaker 192 can provide audio to accompany one or more instructional videos that can be displayed on the display 172.

The pump assembly 160 can be configured to provide easy access (such as, an access door on the casing of the pump assembly) to one or more filters of the pump assembly 160, such as antibacterial filters. This can enable a user (such as, a healthcare provider or patient) to more easily access, inspect or replace such filters. The pump assembly 160 can also include a power jack 196 for providing power to the pump assembly 160 or for charging and recharging an internal power source (such as, a battery). Some implementations of the pump assembly 160 can include a disposable or renewable power source, such as one or more batteries, so that no power jack is needed. The pump assembly 160 can have a recess 198 formed therein to facilitate gripping of the pump assembly 160.

The canister 162 can hold fluid aspirated from the wound 104. For example, the canister 162 can have an 800 mL (or approximately 800 mL) capacity, or from a 300 mL or less capacity to a 1000 mL or more capacity, or any capacity level in this range. The canister 162 can include a tubing for connecting to the conduit 108' in order to form a fluid flow path. The canister 162 can be replaced with another canister, such as when the canister 162 has been filled with fluid. With reference to FIG. 2A, the wound therapy device 110' can include a canister inlet tube 200 (also referred to herein as a dressing port connector) in fluid communication with the canister 162. For example and without limitation, the canister inlet tube 200 can be used to connect with the conduit 108'.

The canister 162 can be selectively coupleable and removable from the pump assembly 160. With reference to FIG. 2A, in some cases, a canister release button 202 can be configured to selectively release the canister 162 from the pump assembly 160. With reference to FIG. 2B, the canister 162 can have one or more fill lines or graduations 204 to indicate to the user and amount of fluid or exudate stored within the canister 162.

The wound therapy device 110' can have a handle 208 that can be used to lift or carry the wound therapy device 110'. The handle 208 can be coupled with the pump assembly 160 and can be rotatable relative to the wound therapy device 110' so that the handle can be rotated upward for lifting or carrying the wound therapy device 110' or the pump assembly 160, or rotated into a lower profile in a more compact position when the handle is not being used. In some cases, the handle 208 can be coupled with the pump assembly 160 in a fixed position. The handle 208 can be coupled with an upper portion of the pump assembly 160 or can be removable from the wound therapy device 110'.

Figure 3:
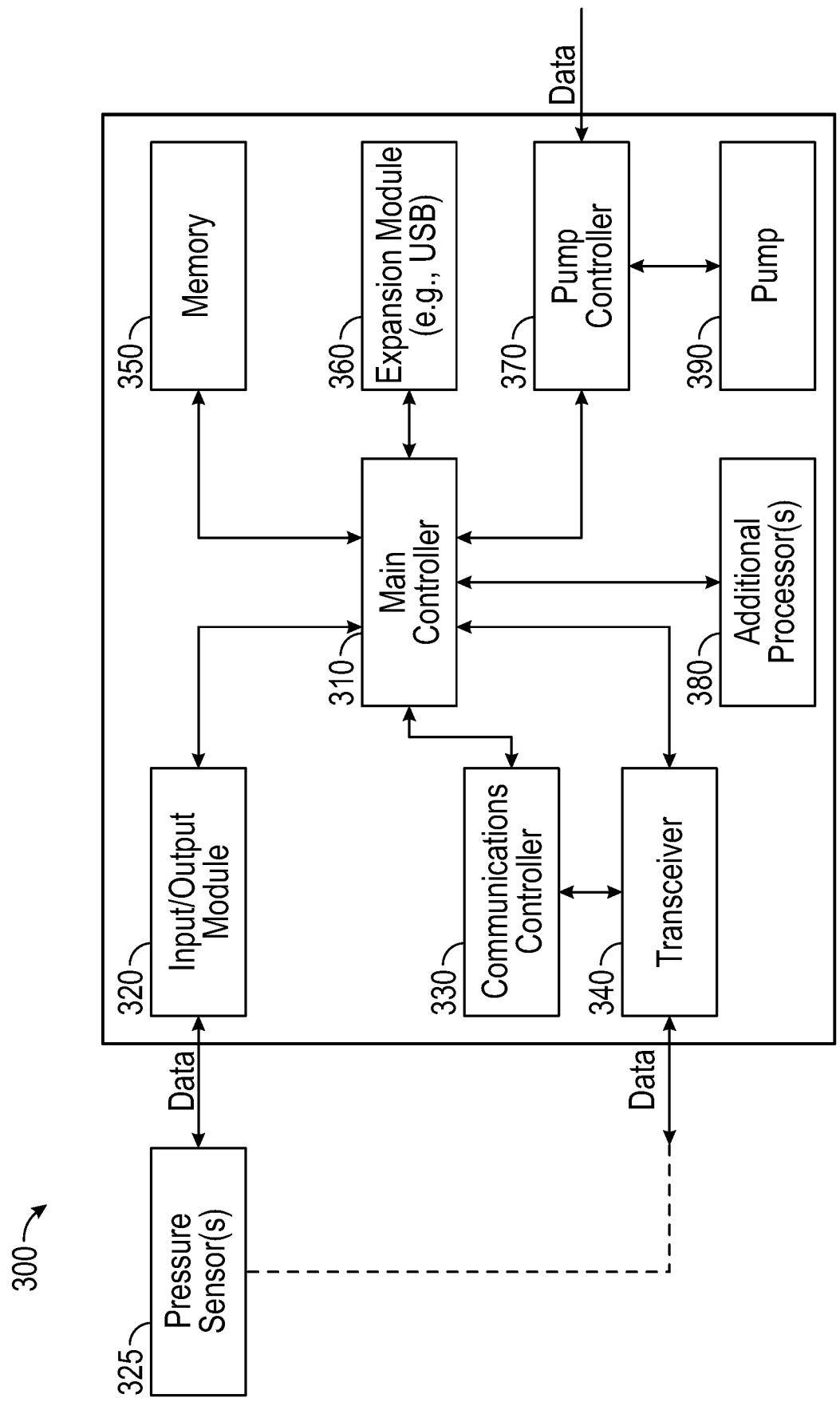
FIG. 3 illustrates a schematic of a control system of a negative pressure wound therapy device.

FIG. 3 illustrates a schematic of a control system 300 that can be employed in any of the wound therapy devices described herein, such as in the wound therapy device 110'. Electrical components can operate to accept user input, provide output to the user, operate the pressure source, provide connectivity, and so on. A first processor (such as, a main controller 310) can be responsible for user activity, and a second processor (such as, a pump controller 370) can be responsible for controlling another device, such as a pump 390.

An input/output (I/O) module 320 can be used to control an input and/or output to another component or device, such as the pump 390, one or more sensors (for example, one or more pressure sensors 325 configured to monitor pressure in one or more locations of the fluid flow path), or the like. For example, the I/O module can receive data from one or more sensors through one or more ports, such as serial (for example, I2C), parallel, hybrid ports, and the like. Any of the pressure sensors can be part of the wound therapy device or the canister. In some cases, any of the pressure sensors 325 can be remote to the wound therapy device, such as positioned at or near the wound (for example, in the dressing or the conduit connecting the dressing to the wound therapy device). In such implementations, any of the remote pressure sensors can communicate with the I/O module over a wired connection or with one or more transceivers 340 over a wireless connection.

The main controller 310 can receive data from and provide data to one or more expansion modules 360, such as one or more USB ports, SD ports, Compact Disc (CD) drives, DVD drives, FireWire ports, Thunderbolt ports, PCI Express ports, and the like. The main controller 310, along with other controllers or processors, can store data in memory 350 (such as one or more memory modules), which can be internal or external to the main controller 310. Any suitable type of memory can be used, including volatile or non-volatile memory, such as RAM, ROM, magnetic memory, solid-state memory, Magnetoresistive random-access memory (MRAM), and the like.

The main controller 310 can be a general purpose controller, such as a low-power processor or an application specific processor. The main controller 310 can be configured as a "central" processor in the electronic architecture of the control system 300, and the main controller 310 can coordinate the activity of other processors, such as the pump controller 370, one or more communications controllers 330, and one or more additional processors 380. The main controller 310 can run a suitable operating system, such as a Linux, Windows CE, VxWorks, etc.

The pump controller 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump controller 370 can measure pressure in a fluid flow path, using data received from one or more pressure sensors 325, calculate the rate of fluid flow, and control the pump. The pump controller 370 can control the pump actuator (such as, a motor) so that a desired level of negative pressure is achieved in the wound 104. The desired level of negative pressure can be pressure set or selected by the user. The pump controller 370 can control the pump (for example, pump motor) using pulse-width modulation (PWM) or pulsed control. A control signal for driving the pump can be a 0-100% duty cycle PWM signal. The pump controller 370 can perform flow rate calculations and detect alarms. The pump controller 370 can communicate information to the main controller 310. The pump controller 370 can be a low-power processor.

Any of the one or more communications controllers 330 can provide connectivity (such as, a wired or wireless connection 332). The one or more communications controllers 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. Any of the one or more transceivers 340 can function as a communications controller. In such case, the one or more communications controllers 330 can be omitted. Any of the one or more transceivers 340 can be connected to one or more antennas that facilitate wireless communication. The one or more communications controllers 330 can provide one or more of the following types of connections: Global Positioning System (GPS), cellular connectivity (for example, 2G, 3G, LTE, 4G, 5G, or the like), NFC, Bluetooth connectivity (or BLE), radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

Any of the one or more communications controllers 330 can provide dual GPS/cellular functionality. Cellular functionality can, for example, be 3G, 4G, or 5G functionality. The one or more communications controllers 330 can communicate information to the main controller 310. Any of the one or more communications controllers 330 can include internal memory or can utilize memory 350. Any of the one or more communications controllers 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the one or more communications controllers 330, the control system 300 can upload any of the data stored, maintained, or tracked by the control system 300 to a remote computing device, such as the device 334. The control system 300 can also download various operational data, such as therapy selection and parameters, firmware and software patches and upgrades, and the like (for example, via the connection to the device 334). The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Multiple Dressing Negative Wound Therapy

Figure 4:
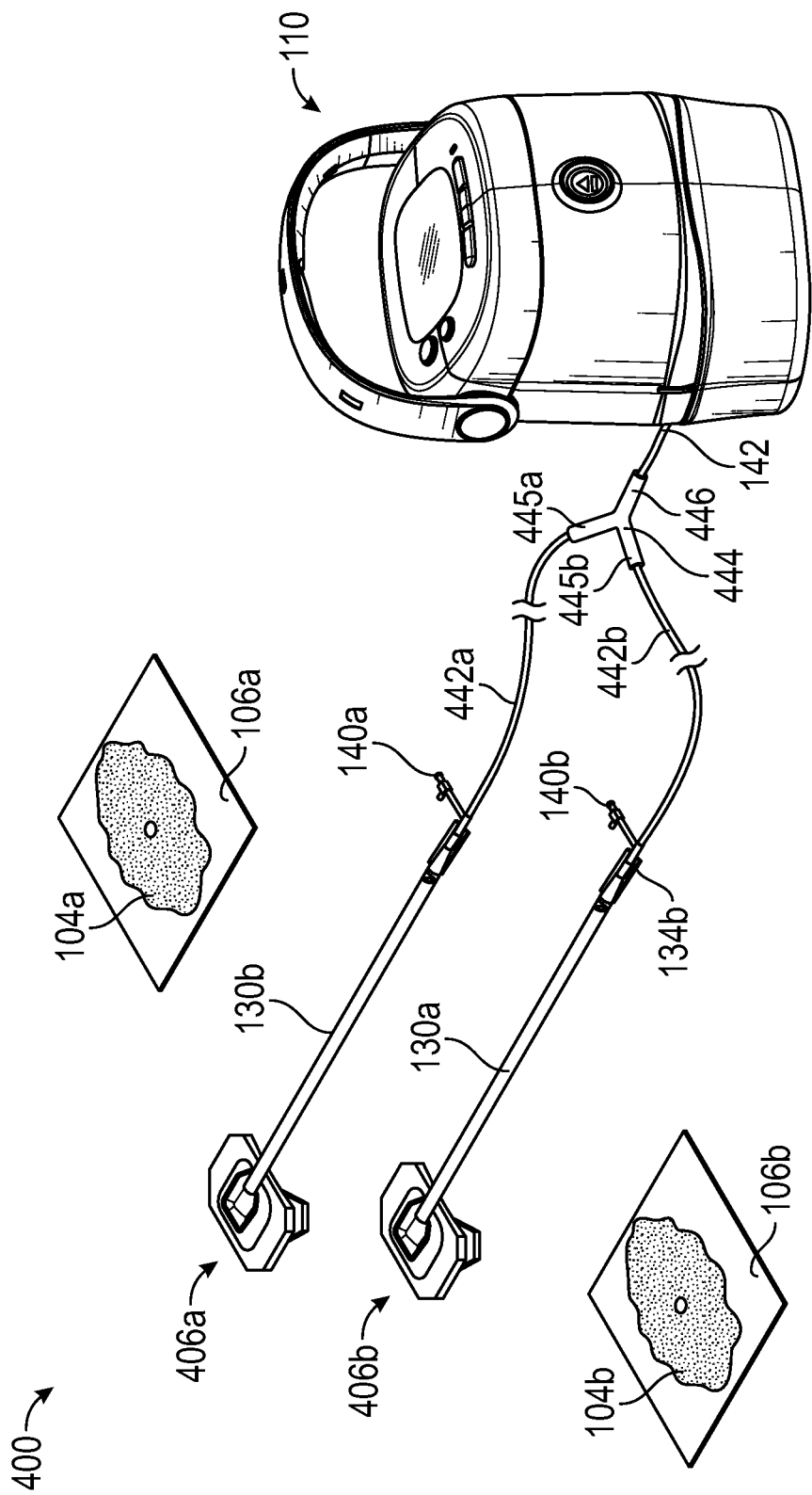
FIG. 4 illustrates another negative pressure wound therapy system.

FIG. 4 illustrates another negative pressure wound treatment system 400. The system 400 can include a wound therapy device capable of supplying negative pressure to the wound site or sites, such as wound therapy device 110'. The wound therapy device 110' can be in fluidic communication with one or more wound dressings 406a, 406b (collectively referred to as 406) so as to supply negative pressure to one or more wounds, such as the wounds 104a and 104b. A first fluid flow path can include components providing fluidic connection from the wound therapy device 110' to the first wound dressing 406a. As a non-limiting example, the first fluid flow path can include the path from the wound dressing 406a to the wound therapy device 110' or the path from the first wound dressing 406a to an inlet 446 of a branching attachment (or connector) 444 in fluidic connection with the wound therapy device 110'. Similarly, a second fluid flow path can include components providing fluidic connection from the wound therapy device 110' to the second wound dressing 406b.

The system 400 can be similar to the system 100' with the exception that multiple wounds 104a and 140b are being treated by the system 400. The system 400 can include any one or more of the components of the system 100', which are illustrated in FIG. 4 with appended letter "a" or "b" to distinguish between the first and second wounds (such as, the wounds 104a and 104b, the covers 106a and 106b). As illustrated, the system 400 can include a plurality of wound dressings 406a, 406b (and corresponding fluid flow paths) in fluidic communication with the wound therapy device 110' via a plurality of suction adapters, such as the adapter 108'. The suction adapters can include any one or more of the components of the adapter 108', which are illustrated in FIG. 4 with appended letter "a" or "b" to distinguish between the first and second wounds (such as, the bridge portions 130a and 130b, the connectors 134a and 134b, and the caps 140a and 140b).

The wound therapy device 110' can be fluidically coupled via the tube 142 with the inlet 446 of the connector 444. The connector 444 can be fluidically coupled via branches 445a, 445b and tubes or conduits 442a, 442b with the connectors 134a, 134b, which can be fluidically coupled with the tubes or conduits 130a, 130b. The tubes or conduits 130a, 130b can be fluidically coupled with the dressings 406a, 406b. Once all conduits and dressing components are coupled and operably positioned, the wound therapy device 110' can be activated, thereby supplying negative pressure via the fluid flow paths to the wounds 430a, 430b. Application of negative pressure can be applied until a desired level of healing of the wounds 430 is achieved. Although two wounds and wound dressing are illustrated in FIG. 4, some implementations of the wound therapy device 110' can provide treatment to a single wound (for instance, by closing the unused branch 445a or 445b of the connector 444) or to more than two wounds (for instance, by adding branches to the connector 444).

The system 400 can include one or more features disclosed in U.S. Patent Publication No. 2020/0069850 or International Publication No. WO2018/167199, each of which is incorporated by reference in its entirety.

Multiple Modes for Operating Negative Pressure Source

Any of the negative pressure devices described herein can include a negative pressure source configured to supply negative pressure to the fluid flow path. Negative pressure source can include an actuator configured to move a pump head. For example, in case of positive displacement pumps, the actuator can move a diaphragm(s), vane(s), piston(s), rotor(s), screw(s), or the like. The actuator can be a motor, piezoelectric transducer, voice coil, or the like. As described herein, a negative pressure wound therapy device can include a controller that controls the operation of the actuator to provide negative pressure therapy. The controller can control the operation of the actuator according to one or more modes. For example, the actuator can operate according to proportional-integral (PI) Mode, Pulsed Mode, or a combination thereof. Each of these modes will be described in turn. For simplicity, certain examples disclosed herein reference a motor as the actuator. However, the present disclosure is applicable for operating negative pressure sources having other types of actuators.

PI Mode

PI Mode is a closed-loop control scheme (sometimes referred to as a feedback control scheme) that can calculate an error signal usable to generate a drive signal for the pump motor. In some cases, the error signal is calculated as a difference between an output (such as, measured pressure in the fluid flow path) and a reference input (such as, a target or set point pressure). In this way, a controller can use the error signal to make corrections to the drive signal applied to the pump motor, which can regulate the pressure supplied by negative pressures source. Example closed-loop control schemes include, but are not limited to, proportional-integral-derivative (PID) control schemes and proportional-integral (PI) control schemes. It will be understood that PI Mode can include any closed-loop control scheme and should not be limited to a proportional-integral (PI) or proportional-integral-derivate (PID) control scheme. In PI Mode, the drive signal for the motor can be continuously (or periodically, such as every millisecond or less or more) generated and the motor can be driven continuously to minimize the error signal.

PI Mode can provide for a smooth drive signal and accurate pressure regulation for achieving the set point. However, in some cases, while operating in PI Mode, the pump motor may be prone to stalling. For example, the motor may stall when the error signal satisfies (such as, falls below) a stall threshold (sometimes referred to as motor-stall-threshold). To satisfy the stall threshold, the error signal can be so small that amount of power proved to the motor is insufficient to turn the motor. For example, as level of negative pressure in the fluid flow path is increasing due to operation of the negative pressure source, the difference between the set point and measured pressure can decrease until eventually the stall threshold is satisfied. Accordingly, in some cases, stalling of the motor can be caused by a low flow condition in the fluid flow path during which level of fluid flow satisfies a low flow threshold indicative of slow flow of fluid. In some instances, low flow condition can be caused by a blockage in the fluid flow path. Stalling of the pump motor can cause the fluid flow to stop and the pressure to fall (for example, as a result of one or more leaks present in the fluid flow path). Eventually, PI Mode can compensate for the drop in pressure by providing the pump motor with a drive signal that no longer satisfies (for example, exceeds the stall threshold), causing the pump motor to restart. In some cases, pump motor can be deactivated before the stall threshold is reached. However, in some cases, driving the pump motor exclusively in PI Mode can cause the pump motor to be stalled and restarted, which can result in one or more of poor pressure regulation, inefficient use of power (for instance, by continuing to supply power to the motor when the motor has stalled), damage to the motor or other components of the negative pressure source, "motor-boating" operation during which the negative pressure source cyclically put into and pulled out of the stall condition, or the like.

Figure 5A:
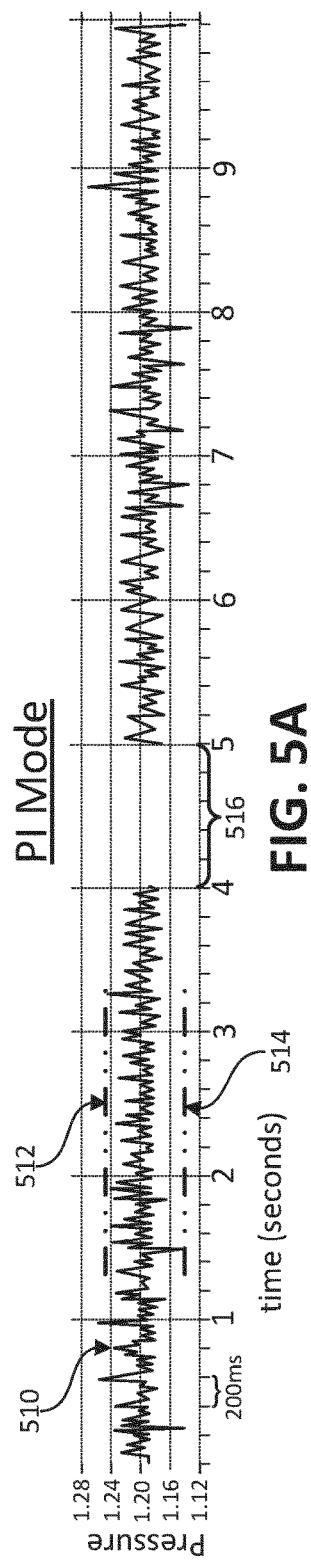
FIG. 5A illustrates a graph representing pressure supplied by an example negative pressure wound therapy device using proportional-integral (PI) control.

FIG. 5A illustrates a graph representing pressure 510 associated with the pump motor operating in an example PI Mode. As is illustrated, the pressure is smoothly regulated within an upper threshold 512 and a lower threshold 514. The upper threshold 512 and the lower threshold 514 can be specified by a negative pressure set point adjusted by a hysteresis limit. Region 516 can correspond to stalling of the pump motor.

Pulsed Mode

In Pulsed Mode, the pump motor can be activated for a duration of time followed by a period of deactivation. This sequence can be repeated. In some cases, Pulsed Mode is a control scheme that uses a pulsed arrangement in which the pump motor is turned on for a first period of time and then is turned off for a second period of time. The pump motor can be controlled at a particular duty cycle (or duration of time the pump motor is active over a particular period of time, such as one minute). Pulsed Mode allows the pump motor to maintain pressure regulation within a specified hysteresis about the set point.

In some cases, Pulsed Mode can overcome at least some of the stall problems associated with PI mode. For example, Pulsed Mode can include driving the pump motor at rated voltage (or current) using a duty cycle determined by the flow rate and the desired hysteresis. In some cases, the pump motor will not be stalled or will stall infrequently in Pulsed Mode. However, in some cases, driving the pump motor according to Pulsed Mode can produce an irritating audible noise, corresponding to the pump motor continuously pulsing on and off. Such noise may be irritating to the user. In addition, the continuous pulsing can cause the pump motor to age prematurely age since starting and stopping can produce greater stress on the mechanical components of the electrical motor and pump head.

Figure 5B:
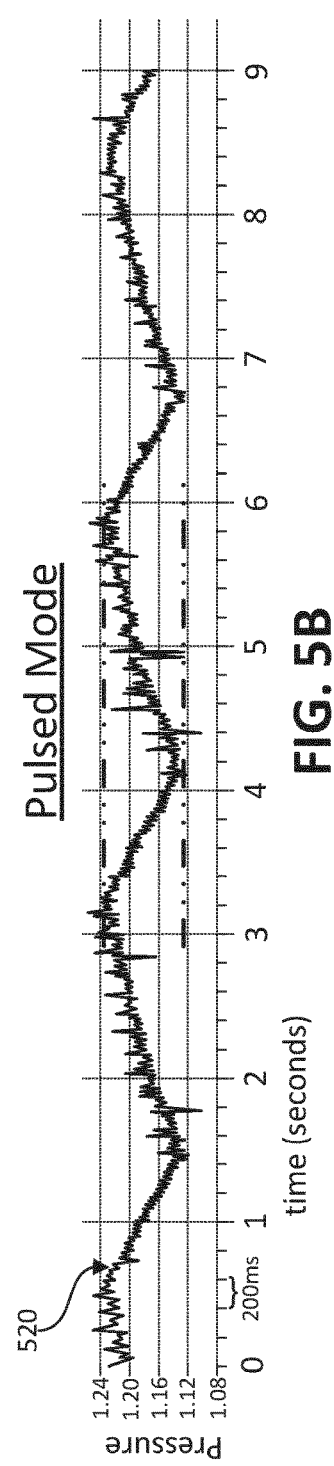
FIG. 5B illustrates a graph representing pressure supplied by an example negative pressure wound therapy device using pulsed control.

FIG. 5B illustrates a graph representing pressure 520 associated with an example Pulsed Mode. The pressure can "bounce" between the upper and lower limits (such as, the upper threshold 512 and the lower threshold 514).

Dual Mode

The pump motor can be controlled to operate in a Dual Mode. For example, the controller can drive the pump motor by dynamically transitioning between Pl mode and Pulsed Mode, as described herein. As an example, the controller can initially drive the pump motor in Pl mode. During PI mode, the controller can iteratively adjust the drive signal to regulate the negative pressure to achieve or maintain the set point. When certain stall conditions are met, the controller can swap and drive the pump motor in Pulsed Mode. During Pulsed Mode, the controller can drive the pump motor in such a way so as to prevent the pump motor from stalling. For example, the controller can drive the pump motor by supplying power above the stall threshold so that the motor would not stall even in the presence of low flow condition. The controller can drive the pump motor by supplying power just above the stall threshold (rather than supplying full or substantially full power) in order to reduce noise. For example, the controller can supply power that is threshold amount of power above (or greater than) the stall threshold.

Operating the pump motor in Dual Mode can combine at least some of the individual advantages of PI mode and Pulsed Mode, while avoiding or lessening at least some of their individual disadvantages. For example, in Dual Mode, the controller can retain a precise control over the pressure in the fluid flow path as provided by the PI Mode, avoid or limit stalling of the pump motor as provided by the Pulsed Mode, avoid or reduce noise associated with the pump motor (by supplying lower amount of power to the motor in Pulsed Mode, switching from Pulsed Mode to PI Mode as soon as possible, etc.), or the like. Advantageously, Dual Mode operation can provide for substantially uninterrupted delivery of negative pressure wound therapy.

Figure 5C:
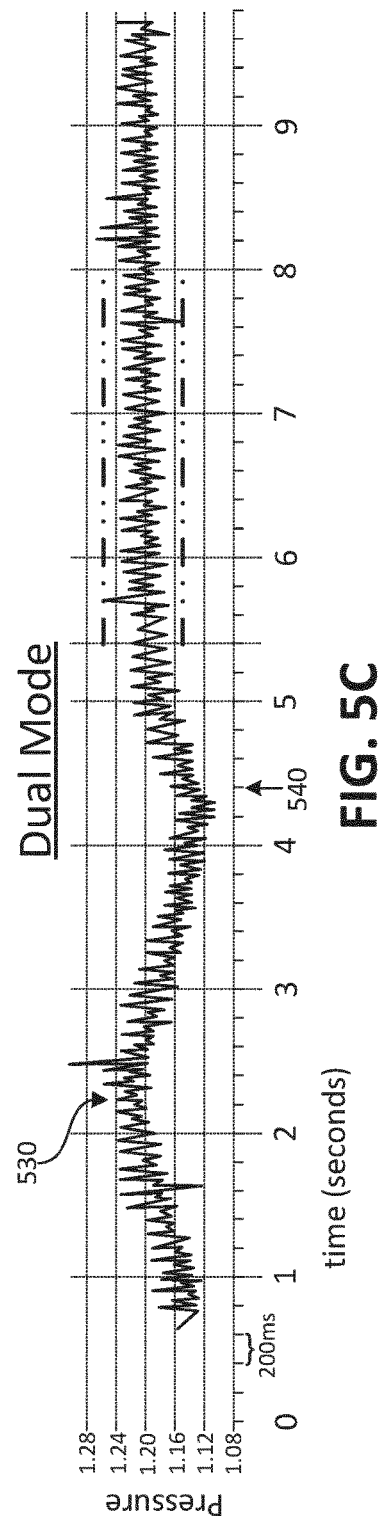
FIG. 5C illustrates a graph representing pressure supplied by an example negative pressure wound therapy device as control transitions from pulsed control to PI control.

FIG. 5C illustrates a graph representing pressure 530 associated with an example Dual Mode, in which the pump motor transitions from Pulsed Mode to PI Mode. In the Pulsed Mode, the voltage (or current) of the pump drive signal can be a fixed low voltage (or current) or PWM drive just above a stall threshold as the pressure rises between about 0.7 to 2.5 seconds. The voltage (or current) of the pump drive signal or PWM drive can be substantially zero between about 2.5 to 4.2 seconds as the pressure falls. At about 4.2 seconds, as the flow increases and the fixed low voltage (or current) pulsed drive or PWM drive becomes insufficient to maintain a negative pressure set point, transition to PI Mode occurs. The transition is illustrated as occurring at 540.

Figure 6:
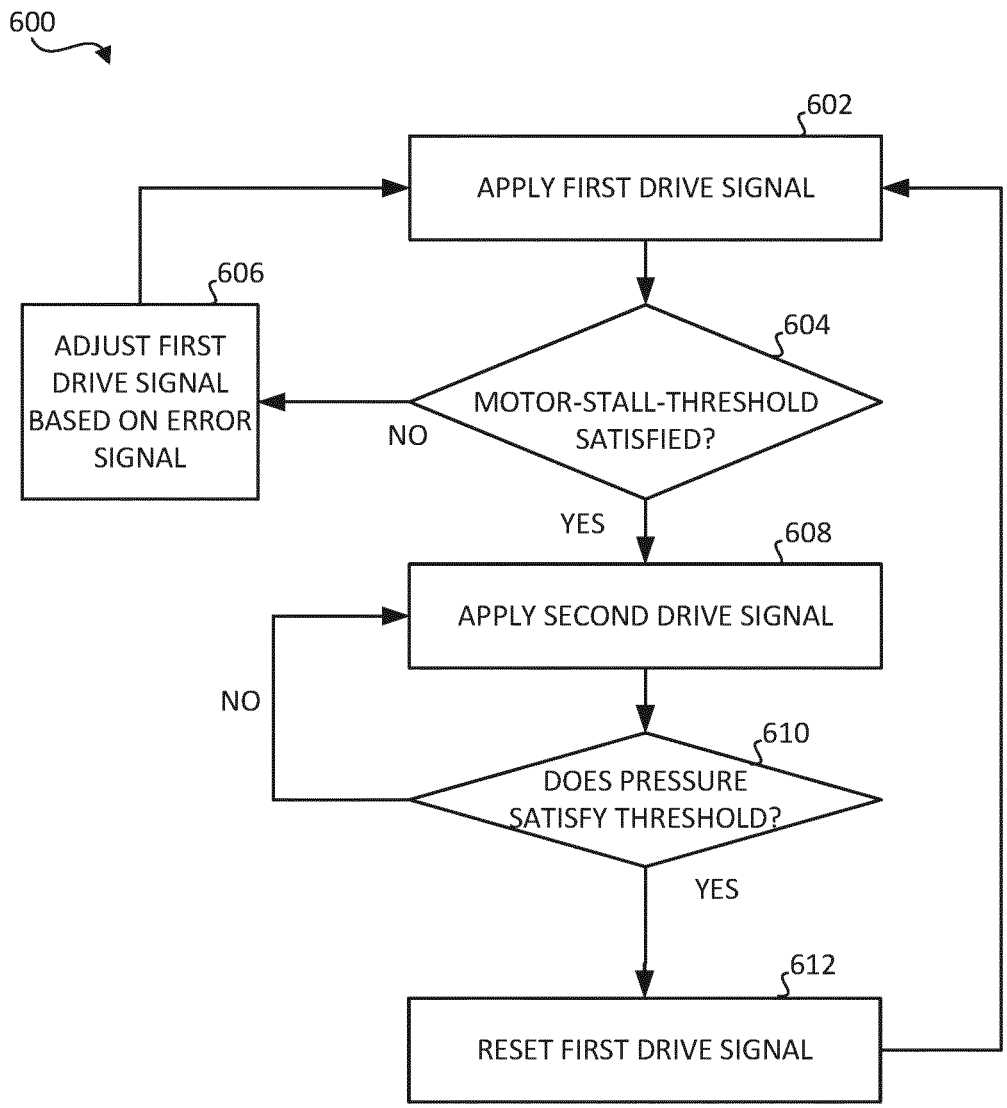
FIG. 6 illustrates a flow diagram of a process for dual mode operation of a negative pressure wound therapy device.

FIG. 6 is a flow diagram of a process 600 for supplying negative pressure to a wound. A negative pressure source can be fluidically connected to the wound dressing, the wound dressing can be positioned to cover at least a portion of the wound, and the negative pressure source can be controlled to supply negative pressure to the wound via the fluid flow path. The process 600 can be implemented by any one or more controllers described herein, such as the pump control processor 370 of FIG. 3. For ease of reference, process 600 has been logically associated as being generally performed by a controller in communication with the negative pressure source, but the following illustrative example should not be construed as limiting.

At block 602, the process 600 can apply a first drive signal to a pump motor of the negative pressure source. In some cases, application of the first drive signal causes the negative pressure source to initiate the supply of negative pressure to the wound via the fluid flow path. In some cases, application of the first drive signal causes the negative pressure source to adjust the supply of negative pressure. For example, as described herein, the first drive signal can be iteratively adjusted to regulate negative pressure against a negative pressure set point. The negative pressure set point can correspond to a desired level of negative pressure and can be pressure set or selected by the user. In some cases, application of the first drive signal indicates, or otherwise corresponds to, a transition to Pl mode, as described herein. The first drive signal can correspond to PI mode because difference between the set point and negative pressure in the fluid flow path can be sufficiently large at the initialization (or restarting) of negative pressure wound therapy such that stalling of the pump motor may not be a significant concern.

The first drive signal (or any of the other drive signals described herein) can be a pulse width modulation (PWM) signal or modulated by another suitable modulation technique. In some cases, the first drive signal (or any of the other drive signals described herein) may not be modulated. For example, the duty cycle of the first drive signal can be any duty cycle between 0-100%. In some cases, the duty cycle of the first drive signal is based on at least one of the voltage (or current) supplied to the pump motor, the set point, or the like. In some cases, the duty cycle of the first drive signal is determined according to the following equation:

$$DrivePWM = SetPressure * k1 + k2 \quad (1)$$

where DrivePWM is the duty cycle of the first drive signal and SetPressure is the set point. Constants $k1$ and $k2$ in Equation 1 can be selected and adjusted for particular type of the pump being controlled. Drive signal determined according to Equation 1 can be supplied to the motor at initialization of negative pressure wound therapy or following a pause in delivery of negative pressure wound therapy. In some cases, DrivePWM in Equation 1 can correspond to an initial PWM (or a motor-stall-threshold). In some instances, Equation 1 can be replaced with a non-linear equation or a look-up table indexed by pressure can be used.

At block 604, the process 600 can identify whether a motor-stall-threshold is satisfied. As described herein, in some cases, operating in PI mode may cause the pump motor to stall. To reduce the likelihood that the motor stalls while operating in PI mode, the process 600 can monitor the motor-stall-threshold and determine when it is satisfied. In some cases, satisfying the motor-stall-threshold indicates that the motor is stalled or that the pump motor will likely stall within a time period if the motor continues operate using its current drive signal (or drive mode). Thus, identifying whether the motor-stall-threshold is satisfied can be a useful indicator in determining if or when the motor is likely to stall. Further, identifying whether the motor-stall-threshold is satisfied can be a useful indicator in determining when to transition from PI mode to Pulsed Mode.

The motor-stall-threshold can correspond to a stall point of the pump motor or to a value just away from the stall point. In some cases, the stall point may be found or determined during testing. For example, if a blockage condition is created in the fluid flow path, then drive signal can be progressively lowered while monitoring power drawing by the motor (for example, motor current). Because a stalled motor may not be turning and may not generate back electromagnetic force (EMF), power drawn by the motor when the motor is stalled may be much higher than power drawn when the motor is running, even when under load. This increase in power can be measured and used to determine or set the motor-stall threshold.

The motor-stall-threshold can be determined in various ways. For example, the motor-stall-threshold can be associated with any combination of one or more of a voltage of a drive signal to the motor, a current of the drive signal, a duty cycle of the drive signal, a pressure at the wound or in the fluid flow path, a torque of the motor, a speed of the motor, back EMF, or the like.

In some implementations, the motor-stall-threshold can be determined based at least in part on a determination that a voltage associated with the drive signal satisfies a voltage threshold indicative of the motor stalling. As an example, if the voltage associated with the drive signal falls below (or, in some cases, exceeds) the voltage threshold, the motor-stall-threshold can be satisfied. The voltage threshold can vary depending on characteristics of the pump or pump motor, design constraints, or the like. For example, in some cases, the motor-stall-threshold can vary based on a static pressure that the pump motor is working against (for example, a higher static pressure can correspond to higher motor-stall-threshold).

In some cases, the motor-stall-threshold can be determined based at least in part on a determination that a current associated with the drive signal satisfies a current threshold. As an example, if the current associated when the drive signal current falls below (or, in some cases, exceeds) the current threshold, the motor-stall-threshold can be satisfied.

As described herein, the current threshold can vary depending on characteristics of the pump or pump motor, design constraints, or the like.

Furthermore, the motor-stall-threshold can be determined based at least in part on a determination that a torque of the pump motor satisfies a torque threshold. As an example, if the torque of the pump motor falls below (or, in some cases, exceeds) the torque threshold, the motor-stall-threshold can be satisfied. As described herein, the torque threshold can vary depending on characteristics of the pump or pump motor, design constraints, or the like. In some cases, the torque threshold is equal to 0 newton-meters (N·m) or some other torque.

In some cases, the motor-stall-threshold can be determined based at least in part on a determination that a duty cycle of the drive signal satisfies a duty cycle threshold. As an example, if the duty cycle associated with the drive signal does not satisfy a duty cycle threshold, the motor-stall-threshold can be satisfied. As described herein, the duty cycle threshold can vary depending on characteristics of the pump or pump motor, design constraints, or the like.

In some cases, the motor-stall-threshold can be determined based at least in part on a determination that a speed of the pump motor satisfies a speed threshold. For example, pump motor speed (for example, measured in revolutions per minute (RPM)), can be determined based on sensor data, such as data from an optical encoder positioned on the pump motor, Hull effect sensor, or the like. In some cases, if the speed of the pump motor falls below (or in some cases, exceeds) the speed threshold, the motor-stall-threshold can be satisfied. As described herein, the duty cycle threshold can vary depending on characteristics of the pump or pump motor, design constraints, or the like. In some cases, the motor-stall-threshold can correspond to absence of back EMF. Stalling of the motor can be determined responsive to detection that the motor produces no back EMF. For instance, back EMF can be determined during a freewheeling mode of operation (such as, when power is not applied to the motor) by measuring the voltage, as described in U.S. Pat. No. 8,494,349 and U.S. Patent Publication No. 2013/0150813, each of which is incorporated by reference in its entirety.

The process 600 can proceed to block 606 if the motor-stall-threshold is not satisfied or to block 608 if the motor-stall-threshold is satisfied.

At block 606, the process 600 can adjust the first drive signal based on the error signal. The process 600 can use the error signal to make corrections to the first drive signal to regulate negative pressure supplied by the pump. In some cases, the duty cycle of the first drive signal is adjusted according to the following equation:

$$\text{Adjusted DrivePWM} = (IGAIN*\text{PressureIntergralError} + PGAIN*\text{PressureError}) \quad (2)$$

where IGAIN corresponds to integral gain (for example, a constant selected for particular pump), PressureIntergralError corresponds to the accumulated error signal (such as, the accumulated PressureError signal), PGAIN corresponds to proportional gain (for example, a constant selected for particular pump), and PressureError corresponds to the error signal. Equation 2 can be used in cases when proportional integral (PI) control is being utilized. The first drive signal as determined using Equation 2 can be applied to the negative pressure source.

In some cases, such as when PID control is used, the duty cycle of the first drive signal is adjusted according to the following equation:

$$\text{Adjusted DrivePWM} = (IGAIN*\text{PressureIntergralError} + PGAIN*\text{PressureError} + DGAIN*\text{PressureDifferentialError}) \quad (3)$$

where DGAIN corresponds to differential gain (for example, a constant selected for particular pump), PressureDifferentialError corresponds to derivative of the error signal, and IGAIN, PressureIntergralError, PGAIN and PressureError are described in connection with Equation 2. The first drive signal as determined using Equation 3 can be applied to the negative pressure source.

In some cases, the error signal is based on a pressure difference between a negative pressure set point corresponding to desired negative pressure at the wound and measured pressure in the fluid flow path (or at the wound). However, it will be understood that metrics other than measured pressure can be utilized to determine the error signal. For example, as illustrated in FIG. 5A, in some cases a voltage (or current) of the drive signal can be proportional to the pressure at the wound. In some such cases, the process 600 can adjust the first drive signal based on voltage (or current) of the drive signal.

In some cases, blocks 602 and 606 can correspond to the pump motor operating in PI mode. For example, in blocks 602 and 606, the process 600 can iteratively adjust the drive signal to regulate the negative pressure against a negative pressure set point. In this way, the pressure regulation to achieve or maintain the set point can be substantially accurate and the pump drive can be smooth, as described herein.

At block 608, responsive to determining that the motor-stall-threshold has been satisfied, the process 600 can apply a second drive signal in lieu of the first drive signal. The second drive signal can cause the motor to operate in Pulsed Mode. The second drive signal can be associated with a suitable duty cycle, as described herein.

The process 600 can transition from block 608 to block 610. At block 610, the process 600 can determine whether control can be switched to PI Mode. As described herein, in Pulsed Mode, the motor can be controlled by alternating periods of activation and deactivation of the motor. As a result, due to one or more leaks present in the fluid flow path, reduction (or loss) of negative pressure may occur. This can lead to increase in the error signal and lessening the likelihood of stalling the motor in PI Mode.

In block 610, the process 600 can determine if measured pressure satisfies a pressure threshold associated with switching to PI Mode. The pressure threshold can be set to a suitable pressure value that is more positive than the lowest expected negative pressure in Pulsed Mode. For example, in Pulsed Mode, the process 600 can maintain pressure in the fluid flow path (or at the wound) in a range defined by maximum and minimum levels of negative pressure. In such example, the pressure threshold can be set to a negative pressure value that is lower than the minimum level of negative pressure.

In some cases, as described herein, at block 610 the process 600 can utilize one or more of error signal, power supplied to the motor (such as, voltage or current), torque of the motor, speed of the motor, back EMF, or the like to determine whether control should be switched to PI Mode.

At block 610, the process 600 can transition back to block 608 in response to determining that the pressure threshold is not satisfied. For example, the process 600 can transition to block 608 in response to determining that the measured pressure is more negative than the pressure threshold. If the pressure threshold is satisfied, the process 600 can transition to block 612.

At block 612, the process 600 can reset the first drive signal to provide a smooth transition from Pulsed Mode to PI Mode. For example, smooth transition can result in no overshoot in negative pressure being supplied to the wound. This can be achieved by resetting the first drive to a level just above the stall threshold. In some cases, the process 600 can reset the first drive signal to the duty cycle determined by Equation 1.

The process 600 can transition from block 612 to block 602, where first drive signal can be supplied to the motor.

It will be understood that the various blocks of FIG. 6 can be implemented in a variety of orders, and that the process 600 may implement one or more of the blocks concurrently and/or change the order, as desired. Furthermore, it will be understood that fewer, more, or different blocks can be used as part of the process 600. For example, process 600 may begin in block 608 instead of block 602.

Any of the negative pressure wound therapy devices described herein can include one or more features disclosed in U.S. Pat. No. 8,308,714, which is incorporated by reference in its entirety.

Other Variations

Although some embodiments describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above,"

"below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A negative pressure wound therapy device comprising:
   a source of negative pressure configured to be connected via a fluid flow path to a wound covered by a wound dressing, the source of negative pressure configured to supply negative pressure to the wound via the fluid flow path;
   a pressure sensor configured to measure pressure in the fluid flow path; and
   a controller configured to control the source of negative pressure, the controller further configured to:
      determine a pressure difference between a negative pressure setpoint corresponding to desired negative pressure at the wound and pressure measured by the pressure sensor;
      in response to determining that the pressure difference does not satisfy a stall threshold of a motor of the source of negative pressure, apply to the motor a first drive signal determined based on the pressure difference; and
      in response to determining that the pressure difference satisfies the stall threshold of the motor, apply a second drive signal to the motor and cause the motor to be activated for a first period of time and deactivated for a second period of time subsequent to the first period of time.

2. The negative pressure wound therapy device of claim 1, wherein the first drive signal causes the motor to operate in accordance with at least one of a proportional integral (PI) control or proportional integral derivative (PID) control.

3. The negative pressure wound therapy device of claim 2, wherein the second drive signal causes the motor to operate in accordance with pulsed control.

4. The negative pressure wound therapy device of claim 1, wherein the first drive signal causes the motor to be activated for a duration of the first drive signal.

5. A negative pressure wound therapy device comprising:
   a source of negative pressure configured to be connected via a fluid flow path to a wound covered by a wound dressing, the source of negative pressure configured to supply negative pressure to the wound via the fluid flow path;
   a pressure sensor configured to measure pressure in the fluid flow path; and
   a controller configured to control the source of negative pressure, the controller further configured to:
      responsive to a determination that a pressure difference between a desired level of negative pressure at the wound and pressure measured by the pressure sensor does not satisfy a stall threshold of a motor of the source of negative pressure, actuate the motor according to a proportional integral (PI) control or proportional integral derivative (PID) control; and
      responsive to a determination that the pressure difference satisfies the stall threshold of the motor, actuate the motor according to a pulsed control.

6. The negative pressure wound therapy device of claim 5, wherein the stall threshold of the motor corresponds to a voltage or current level causing the motor to stall.

7. The negative pressure wound therapy device of claim 5, wherein pulsed control comprises alternating periods of activation and deactivation of the motor.

8. A negative pressure wound therapy device comprising:
   a source of negative pressure configured to be connected via a fluid flow path to a wound covered by a wound dressing, the source of negative pressure configured to supply negative pressure to the wound via the fluid flow path;
   a pressure sensor configured to monitor a pressure in the fluid flow path; and
   a controller configured to control the source of negative pressure, the controller further configured to:
      apply a first drive signal to an actuator of the source of negative pressure to cause the source of negative pressure to supply negative pressure to the wound via the fluid flow path;
      adjust the first drive signal applied to the actuator based on a difference between the pressure in the fluid flow path and a negative pressure setpoint; and
      responsive to a determination that a flow in the fluid flow path satisfies a flow threshold indicative of a stalling of the actuator, apply a second drive signal different from the first drive signal to the actuator and cause the actuator to continue operating to establish or maintain the negative pressure setpoint at the wound.

9. The negative pressure wound therapy device of claim 8, wherein the controller is configured to adjust the first drive signal to minimize the difference between the pressure in the fluid flow path and the negative pressure setpoint.

10. The negative pressure wound therapy device of claim 8, wherein the controller is further configured to determine that the flow threshold is satisfied responsive to the difference satisfying a pressure difference threshold.

11. The negative pressure wound therapy device of claim 8, wherein the controller is configured to iteratively adjust the first drive signal.

12. The negative pressure wound therapy device of claim 8, wherein the controller is further configured to:
responsive to a determination that the pressure in the fluid flow path is smaller than a pressure threshold, cease applying the second drive signal and apply the first drive signal to the actuator.

13. The negative pressure wound therapy device of claim 8, wherein the controller is further configured to cease applying the second drive signal and apply the first drive signal responsive to a determination that the flow threshold is no longer satisfied.

14. The negative pressure wound therapy device of claim 8, wherein the controller is further configured to:
responsive to a determination that the pressure in the fluid flow path does not satisfy the negative pressure setpoint, continue to adjust the first drive signal based on the difference.

15. The negative pressure wound therapy device of claim 8, wherein the first drive signal causes the actuator to operate in accordance with at least one of a proportional integral (PI) control or proportional integral derivative (PID) control.

16. The negative pressure wound therapy device of claim 15, wherein the second drive signal causes the actuator to operate in accordance with pulsed control that alternates periods of activation and deactivation of the actuator.

17. The negative pressure wound therapy device of claim 8, wherein the actuator comprises a motor.

18. The negative pressure wound therapy device of claim 8, wherein the controller is configured to apply the second drive signal at a power level that is less than maximum power level of the actuator.

19. The negative pressure wound therapy device of claim 8, wherein the actuator comprises a motor, and wherein application of the first drive signal responsive to the determination that the flow in the fluid flow path satisfies the flow threshold would cause the motor to stall.

20. The negative pressure wound therapy device of claim 1, wherein application of the first drive signal in response to determining that the pressure difference satisfies the stall threshold would cause the motor to stall.

21. The negative pressure wound therapy device of claim 5, wherein actuation of the motor responsive to the determination that the pressure difference satisfies the stall threshold of the motor would cause the motor to stall.

* * * * *